US011627933B2

United States Patent
Zhang et al.

(10) Patent No.: US 11,627,933 B2
(45) Date of Patent: Apr. 18, 2023

(54) RING-ARRAYED FORWARD-VIEWING ULTRASONIC IMAGING SYSTEM AND METHOD WITH NEEDLE GUIDANCE AND IMAGE RECONSTRUCTION

(71) Applicant: Worcester Polytechnic Institute, Worcester, MA (US)

(72) Inventors: Haichong Zhang, Shrewsbury, MA (US); Ryosuke Tsumura, Worcester, MA (US); Yichuan Tang, Millbury, MA (US)

(73) Assignee: Worcester Polytechnic Institute, Worcester, MA (US)

( * ) Notice: Subject to any disclaimer, the term of this patent is extended or adjusted under 35 U.S.C. 154(b) by 0 days.

(21) Appl. No.: 17/083,776

(22) Filed: Oct. 29, 2020

(65) Prior Publication Data

US 2021/0128103 A1 May 6, 2021

Related U.S. Application Data

(60) Provisional application No. 63/077,340, filed on Sep. 11, 2020, provisional application No. 62/927,967, filed on Oct. 30, 2019.

(51) Int. Cl.
*A61B 8/00* (2006.01)
*A61B 8/08* (2006.01)
*A61B 8/12* (2006.01)

(52) U.S. Cl.
CPC .............. *A61B 8/0841* (2013.01); *A61B 8/12* (2013.01); *A61B 8/42* (2013.01); *A61B 8/488* (2013.01); *A61B 8/5207* (2013.01); *A61B 8/5246* (2013.01)

(58) Field of Classification Search
CPC .......... A61B 8/0841; A61B 8/12; A61B 8/42; A61B 8/488; A61B 8/5207; A61B 8/5246
See application file for complete search history.

(56) References Cited

U.S. PATENT DOCUMENTS

| | | | |
|---|---|---|---|
| 2009/0105597 A1* | 4/2009 | Abraham | A61B 8/08 600/466 |
| 2011/0098572 A1 | 4/2011 | Chen et al. | |
| | | (Continued) | |

FOREIGN PATENT DOCUMENTS

| | | |
|---|---|---|
| WO | 2017139728 A1 | 8/2017 |
| WO | 2017205808 A1 | 11/2017 |

OTHER PUBLICATIONS

International Search Report, PCT/US2020/057892, dated Feb. 18, 2021, pp. 7.

*Primary Examiner* — Serkan Akar
*Assistant Examiner* — Amal Aly Farag
(74) *Attorney, Agent, or Firm* — Armis IP Law, LLC

(57) ABSTRACT

A Ring-Arrayed Forward-viewing (RAF) ultrasound imaging and administration device combines an ultrasonic (US) US imager including a plurality of single element transducers arranged in a circular frame to define a ring array, and an instrument posture tracking circuit coupled to the ring array for performing RF (radio frequency) data acquisition with the plurality of ring-arrayed transducers. A needle holster is concentrically disposed in the ring array and is adapted to receive and direct an insertion instrument such as a needle, probe or extraction tool along an axis defined by a center of the ring array directed by the concentric needle holster. The tracking circuit includes a processor having instructions for instrument posture tracking and US imaging.

17 Claims, 9 Drawing Sheets

(56) References Cited

U.S. PATENT DOCUMENTS

2012/0259204 A1* 10/2012 Carrat ................. A61B 6/12
                                                     600/414
2018/0296194 A1* 10/2018 Yamanaka ............ A61B 8/085

* cited by examiner

RING-ARRAYED FORWARD-VIEWING ULTRASONIC IMAGING SYSTEM AND METHOD WITH NEEDLE GUIDANCE AND IMAGE RECONSTRUCTION

RELATED APPLICATIONS

This patent application claims the benefit under 35 U.S.C. § 119(e) of U.S. Provisional Patent App. No. 62/927,967, filed Oct. 30, 2019, entitled "RING-ARRAYED ULTRASONIC IMAGING," and on U.S. Provisional Patent App. No. 63/077,340, filed Sep. 11, 2020, entitled "INSERTION SITE ULTRASONIC IMAGING," both incorporated herein by reference in entirety.

STATEMENT OF FEDERALLY SPONSORED RESEARCH AND DEVELOPMENT

This invention was made with government support under grant DP5 OD028162, awarded by the National Institute for Health (NIH). The government has certain rights in the invention

BACKGROUND

Medical imaging provides diagnostic views of anatomical structures in a noninvasive manner. Anatomical structures may be identified and assessed prior to any kind of invasive procedure. Such technologies generally involve a propagated wave medium that reflects or refracts off anatomical features for qualitative assessment thereof. Typical imaging technologies include Ultrasound (US), CAT (Computer Assisted Tomography), MRI (Magnetic Resonance Imaging) and X-Ray, each having various features and costs. In particular, ultrasound is beneficial for low cost, portability, and a benign waveform medium that is acceptable in delicate environments such as pregnancy.

SUMMARY

A registration-free ultrasound-guided needle intervention assistance device allows for viewing of ultrasound images synchronized with the needle insertion motion. A concentric ring array disposes ultrasound (US) transducers in a circular arrangement around an insertion site, while an acoustic mirror reflects US signals to focus the signal for direct alignment with the insertion site and needle path. A Ring-Arrayed Forward-viewing (RAF) ultrasound imaging system includes a circular ring array of transducers defined by a frame having an open hole or region inside the ring where a percutaneous needle may be inserted.

The use of a circular array provides a forward-viewing US image and needle visualization at the center of the reconstructed image without additional registration. The overall system include a radio frequency (RF) data acquisition receiver for B-mode image reconstruction along the direction of forward needle insertion based on the acquired RF data with a back-propagation method. Acoustically reflective mirrors disposed on or near the insertion site at the center of the array provide additional signal feedback along the needle axis.

Configurations herein are based, in part, on the observation that ultrasound imaging has benefits over other imaging technologies such as CAT (Computer Assisted Tomography), MRI (Magnetic Resonance Imaging) and X-Ray, including cost, size and benign sonic sensing mediums rather than magnetic and radiation mediums which can be harmful to some patients. Unfortunately, conventional approaches to ultrasonic sensing suffer from the shortcoming of imposing manual placement and alignment for invasive procedures such as percutaneous needle insertion for biopsy and other procedures. During such intervention, physicians are required to manipulate the US probe for guiding the direction of needle insertion with their non-dominant hand because the dominant hand guides the biopsy needle, such that the positional relationship between the needle and US images is subject to interpretation by physician's experiences.

Percutaneous needle interventions, such as biopsy or ablation under the guidance of ultrasound imaging, has been a common procedure for diagnosis and treatment of many medical issues. However, conventional ultrasound guided percutaneous needle interventions are highly operator-dependent because of the inherent difficulties in managing hand-eye coordination between the needle and ultrasound transducer to maintain an adequate sonographic window. The ultrasound transducer and needle are two independent entities, and impaired localization and visualization of the needle may result in an increased risk of complications and diminished primary efficacy. Thus, there is an unmet need for an image-guidance device allowing the simple and intuitive needle intervention absent a need for any registration process.

Accordingly, configurations herein substantially overcome the shortcomings of conventional, manual probes by providing a guidance device having a circular array of transducers around a needle insertion sleeve centered in the circular array for defining a position and axis of needle travel relative to the transducers. The resulting needle insertion enjoys a fixed registration with the transducers for allowing visualization of a reconstruction plane along the path of needle insertion. The visualized path is rotatable by an encoder or other engagement with the circular ring array to define both the axial position and relative rotation of a rendered image depicting the insertion path of the needle progressing towards a surgical target.

A system, method and device for generating an image of scanned tissue receives a set of signals from a circular array of transducers, such that the circular array is defined by a circular frame having the transducers disposed thereon. A rotary encoder identifies a reconstruction plane defined by a rotational position of the circular array, and a tracking and imaging circuit generates an image based on the received set of signals by reconstructing, for each of a plurality of positions on the reconstruction plane, a corresponding pixel based on a signal in the set of signals received from each of the transducers on the circular frame.

BRIEF DESCRIPTION OF THE DRAWINGS

The foregoing and other objects, features and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION

Figure 1:
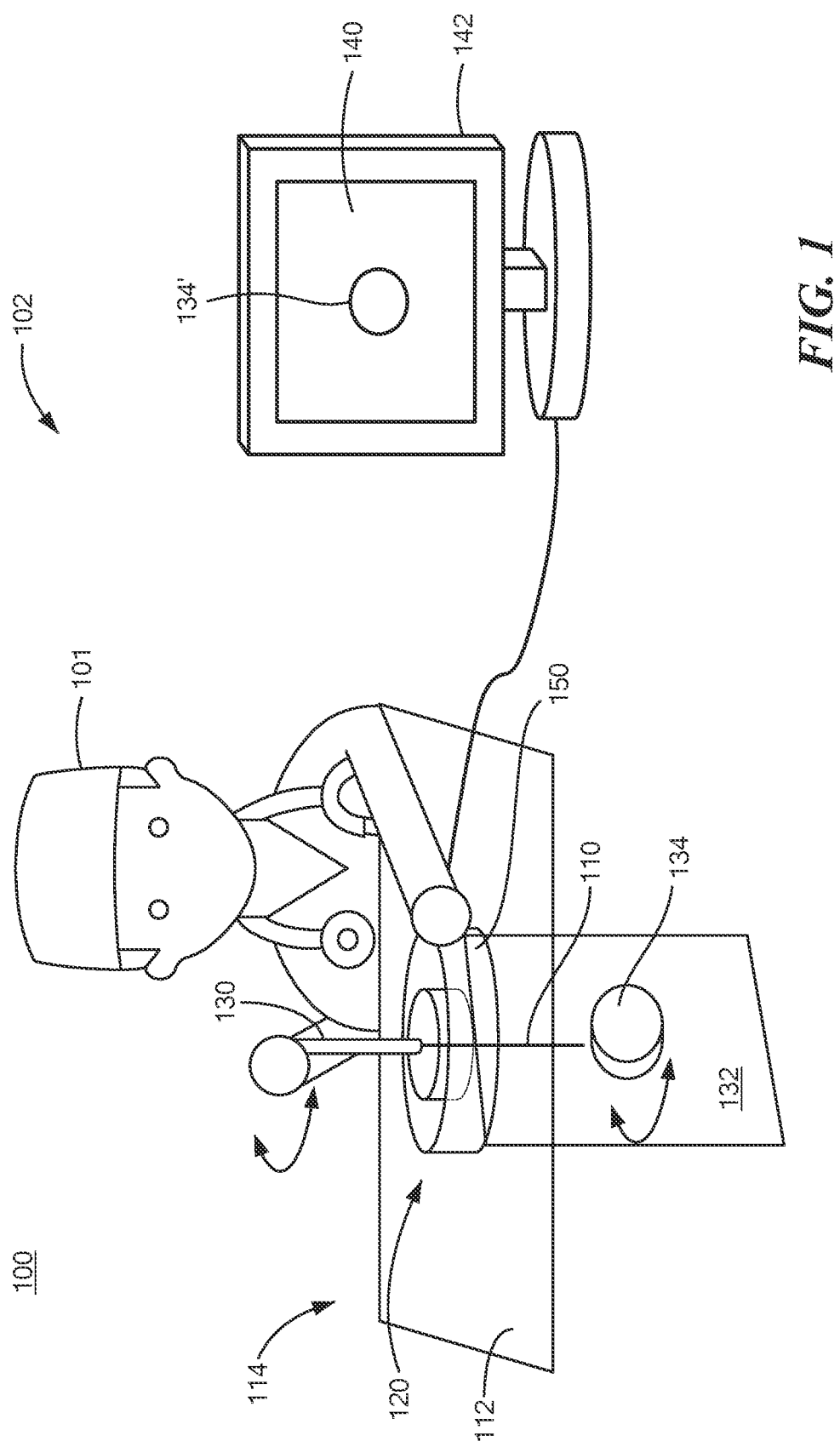
FIG. 1 is a system context diagram of a medical diagnosis environment suitable for use with configurations herein.

The description below presents an example of the RAF device for reconstructing image data defining a plane along an insertion path of a surgical needle, typically a transcutaneous needle in conjunction with an epidermally placed RAF device. FIG. 1 is a system context diagram of a medical diagnosis environment 100 suitable for use with configurations herein. Referring to FIG. 1, an operator 101 such as a doctor, nurse or medical technician operates a needle 110 for insertion. The RAF device for needle insertion (device) 120 rests on an epidermal surface 112 of a patient 114. A rotatable, circular frame 150 rotates for gathering ultrasonic signals depicting a reconstructed plane image 132 including a surgical target 134, for processing and rendering the signals and rendering an image 140 on a monitoring device 142 for visual feedback of needle 110 insertion and aiming towards the surgical target 134. The frame 150 surrounds a sheath 130 centered in the frame 150 for guiding the needle 110 to the surgical target 134.

The monitoring device 142 allows rendering of the image 140 of the surgical target 134, such that the surgical target 134 is located on the reconstruction plane 132 and based on an insertion site aligned with a needle on a trajectory defined by the needle insertion sheath 130. Since the needle path is centered among the transducers, the reconstructed plane image 132 includes the path at any rotation of the reconstructed plane image 132. The surgical target 134 may be, for example, a region or growth for retrieving a biopsy sample, or the reconstructed plane 132 may simply define a diagnostic region for further imaging.

Figure 2A:
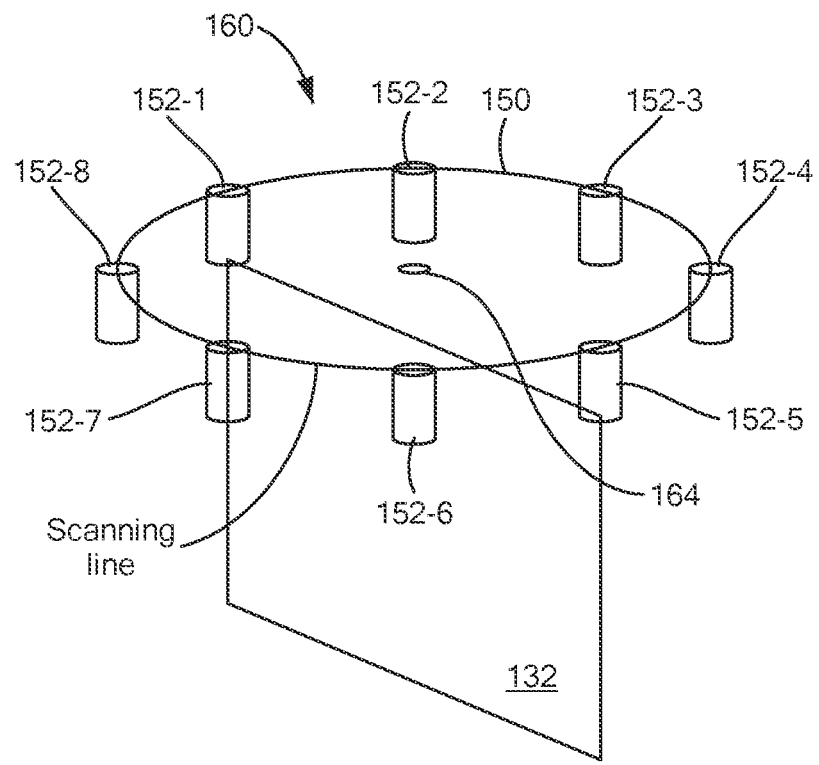
FIGS. 2A and 2B shows a position of the ultrasound (US) transducers in the environment of FIG. 1.
Figure 2B:
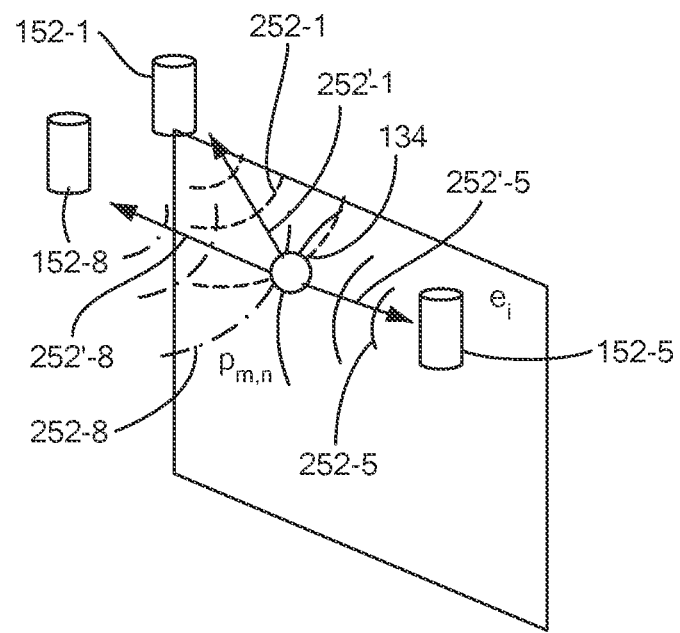

FIGS. 2A and 2B shows a position of the ultrasound (US) transducers in the environment of FIG. 1. Referring to FIGS. 1 and 2, the device 120 includes a circular frame 150 of US transducers (transducers) 152-1 . . . 152-8 (152 generally). Any suitable number of transducers may be employed; 8 are shown for ease of illustration, however an actual RAF array may have around 300 elements, and impose merely that an encoder having sufficient resolution is employed.

The array 160 is employed for a method for generating an image of scanned tissue, which includes receiving a set of signals from a circular array 160 of transducers 152, in which the circular array 160 is defined by the circular frame 150 having the transducers 152 disposed thereon. Based on positional input from an encoder (discussed below), the reconstruction plane 132 is identified, defined by a rotational position of the circular array 160. As shown in FIG. 2B, individual transducers 152-1, 152-8, and 152-5 emit sonic pulses 252-1, 252-8 and 252-5, respectively. The image 140 is generated based on a received set of signals shown by arrows 252'-1 . . . 252'-8 and 252'-5 (252' generally), by reconstructing, for each of a plurality of positions on the reconstruction plane 132, a corresponding pixel based on a signal in the set of signals 252' received from each of the transducers 152.

Identification of the reconstruction plane 132 includes aligning the reconstruction plane with a center 164 of the circular array based on the needle positioning sheath 130 adapted to slidably receive a needle 110 for directing the needle to the target location 134 depicted on the generated image 140. This ensures that the target location and the needle 110 are aligned with the reconstruction plane 132 and visualized on the generated image 140.

Figure 3:
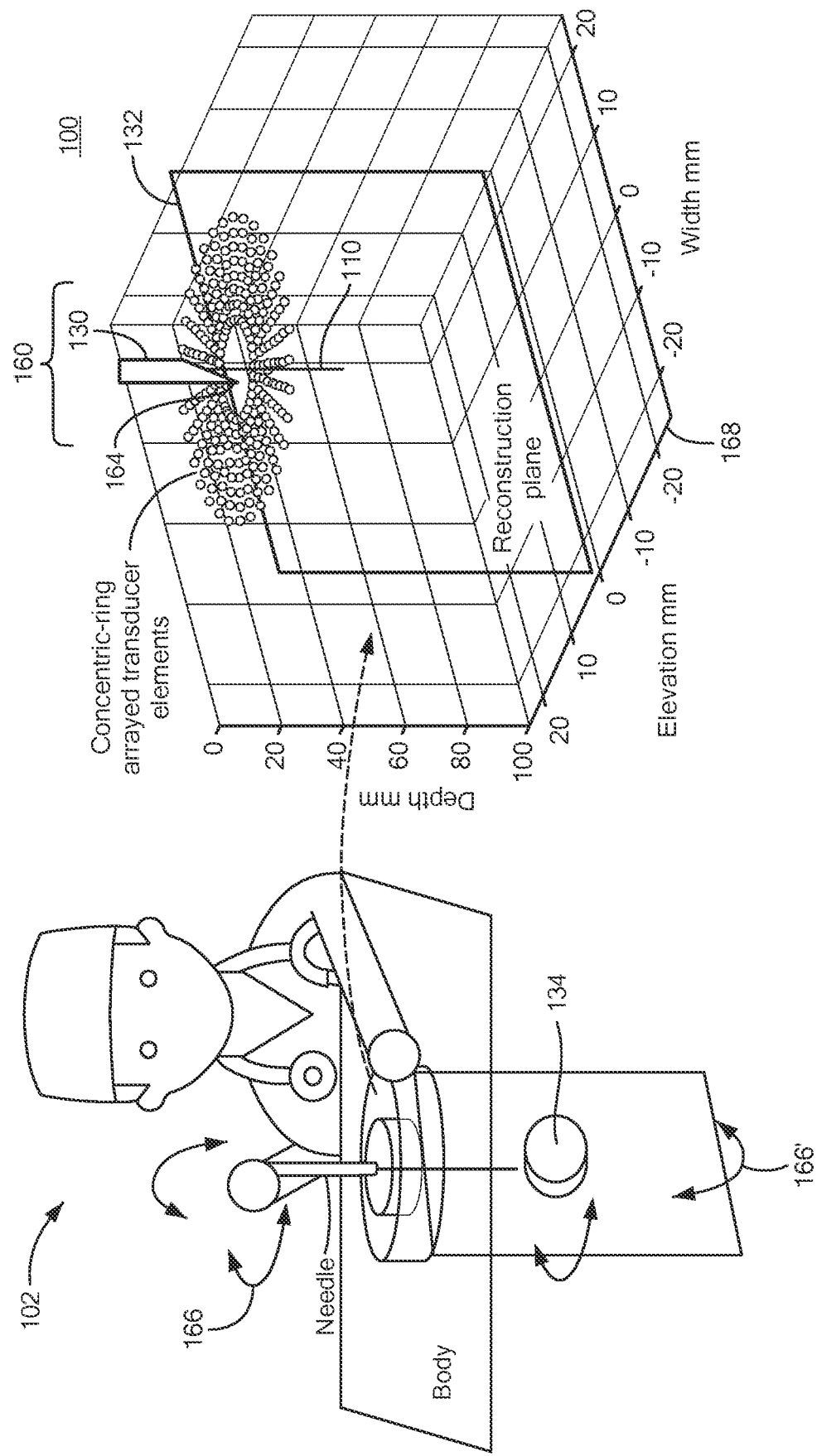
FIG. 3 shows the reconstruction plane for imaging by the transducers of FIGS. 2A and 2B.

FIG. 3 shows the reconstruction plane 132 for imaging by the transducers of FIGS. 2A and 2B. Referring to FIGS. 1-3, the relation of the circular transducer array 160 to the reconstruction plane 132 is shown in the imaging system 102 which tracks insertion of the needle 110 into the center 164 of the transducers 152. to visualize forward-views corresponding to the articulated needle posture by measuring a rotational position 166 based on movement of the frame 150 around the insertion site. Computations based on a coordinate plane 168 and angular values defined by the rotational position compute the rendered image 140 and any surgical targets 134 therein based on the reconstruction plane 132. Horizontal rotation 166' may also be achieved by slightly tilting the sheath 130, discussed further below.

In generating the reconstruction plane and tendering the image 140, transducer signals 252 are emitted and ultrasonic signals returned 252' from the tissue located in the reconstruction plane 132. Generally, the return signals 252 indicate a relative density of tissue which can be depicted in the rendered image 140 as varied shades. Unlike a conventional linear transducer array in a typical hand-held probe, the signals emit and return to the transducers 152 in a circular pattern, which thus varies based on an angle on the frame 150 from which the signals are received.

The return signal from an individual transducer defines a so-called A-mode, or A-line data. A-mode return signals 252' result in a waveform with spikes or peaks at the interface of two different tissues, for example where subcutaneous fat and muscle meet. B-mode scans produce a two-dimensional image of the underlying tissue. The A-mode (amplitude mode) is the simplest type of ultrasound. In A-Mode, a single transducer scans a line through the body with the echoes resulting as a function of depth. In B-mode, sometimes referred to as 2D, a linear array of transducers simultaneously scans a plane through the body that can be viewed as a two-dimensional image on screen.

To visualize the forward-viewing rendered image 140 based on the tracked needle posture, a beamforming technique is employed to reconstruct the US image with RF A-line data acquired by the ring-arrayed single element transducers 152. Synthetic aperture imaging and plane wave imaging are conventional reconstruction methods which can provide sequential US image data one line at a time. For example, both monostatic synthetic aperture and plane wave imaging may be employed to perform simple data acquisition by invoking the same transducer 152 element as a transmitter and a receiver, which can provide effective dynamic range and resolution of the image. Configurations herein extend monostatic synthetic aperture imaging to enable visualization of the forward-viewing rendered image 140 based on the ring-arrayed single element transducers 152.

US signals are transmitted and reflected wave-fronts, defining the A-line RF data, and are received at each transducer 152-N position, thereby an x-z plane B-mode image is formed line by line. Meanwhile, in the ring-array 150, the positional relationship between the reconstructed plane 132 and each transducer 152 position receiving RF A-line data is different from a conventional linear array because of the circular arrangement. Thus, the ring-arrayed positions of the single element transducer 152 can be defined as:

$$e_i = (r\cos(t_i), r\sin(t_i), 0)[0 \leq t_i \leq 2\pi] \quad (1)$$

$$t_i = \frac{2\pi}{L}i[0 \leq i \leq L]$$

Where ei represents the position of i-th transducer in the number of L single element transducers. Also, r represents the radius of the circular array, i.e. frame 150.

In order to incorporate the RF A-line data corrected by the ring-arrayed single element transducers real-time, a back-propagation approach is applied, depicted further in FIG. 5 below. This approach can project the collected A-line data back to the predefined 2D field used for visualizing the targeted slice. The reconstruction with the back-propagation can be formulated as follows:

$$y_{bf}(m, n) = \sum_e y_{bf_e}(m, n, e) \quad (2)$$

$$y_{bf_e}(m, n, e) = y_{pre}(d, e) \quad (3)$$

Where ybf is the total reconstructed RF data, ybfe is the reconstructed RF data from each transducer position, and ypre is the received raw RF data. m and n depict the pixel information of the lateral and axial direction in the reconstruction image, respectively. The distance used when collecting the pre-beamformed data is d, and the transducer position is e. The received signal distance can be calculated with the Euclidean distance between the pixel position of the reconstruction image and transducer position, following:

$$d = \|p_{m,n} - e\| \quad (4)$$

$p_{m,n}$ represents the pixel position of m-by-n matrix in the 3D world coordinate system, which is dependent on the slice angle of reconstruction image in the radial direction. Further, to decrease the effect of side lobes, a coherent factor used as a metric of focusing quality is applied. It is defined as the ratio between the coherent and incoherent sums across the array. The coherent factor performs such that high and low values indicate high- and low-quality image, respectively. By applying the coherent factor to the back-propagation approach, Eq. (2) can be replaced, as follows:

$$y_{bf_{CF}}(m, n) = CF(m, n) \sum_e y_{bf_e}(m, n, e) \quad (5)$$

$$CF(m, n) = \frac{\left|\sum_e y_{bf_e}(m, n, e)\right|^2}{L \sum_e |y_{bf_e}(m, n, e)|^2} \quad (6)$$

Figure 4:
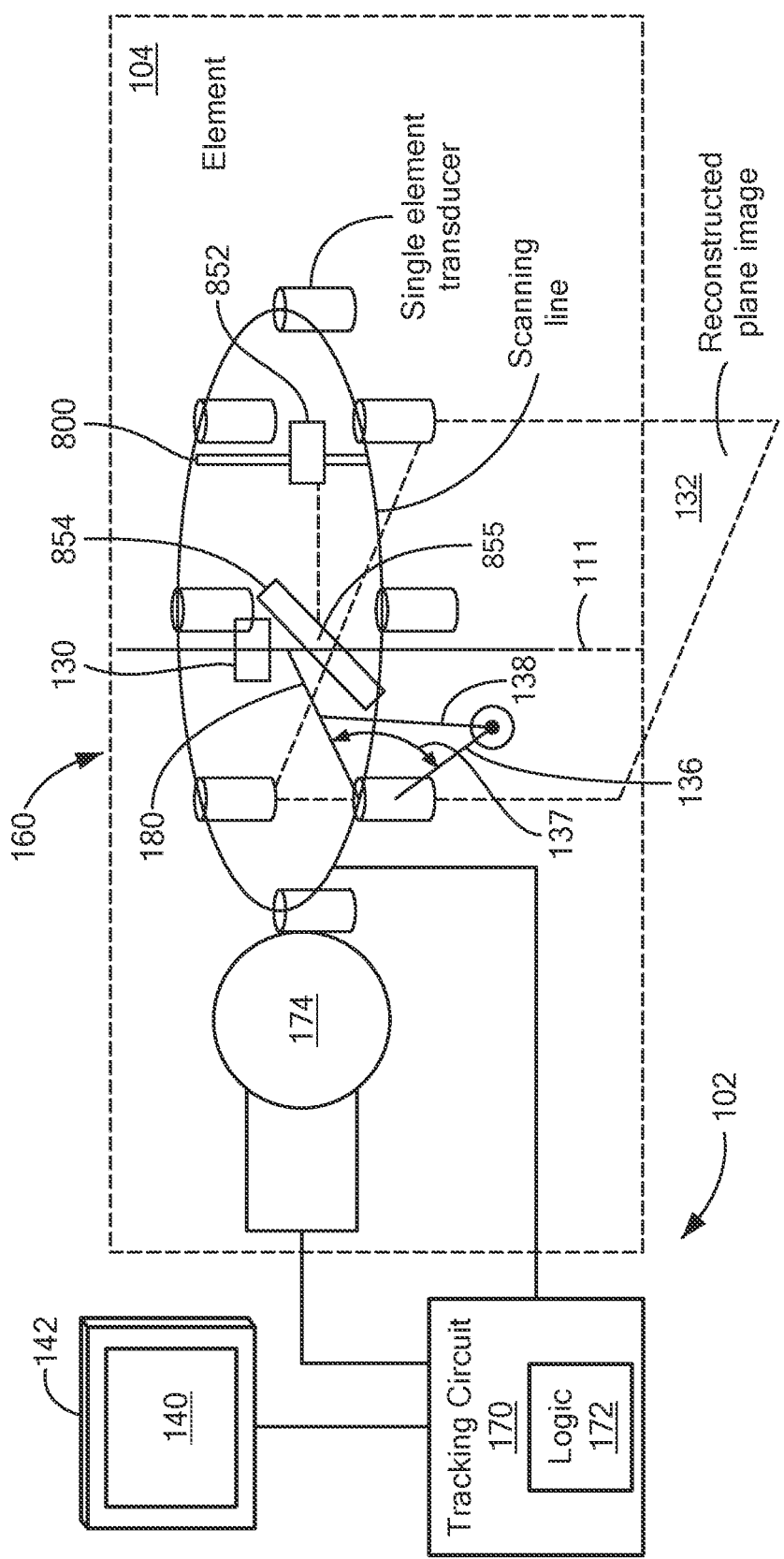
FIG. 4 shows an imaging system using the transducers of FIGS. 2A, 2B and 3 in the environment of FIG. 1.

FIG. 4 shows an imaging system using the transducers of FIGS. 2A, 2B and 3 in the environment of FIG. 1. Referring to FIGS. 1-4, the Ring-Arrayed Forward-viewing (RAF) ultrasound imaging and administration device 102 is shown in further detail. The device 102 includes an ultrasonic (US) US imager 104 including a plurality of single element transducers 152 arranged in the circular frame 150 to define the ring array 160, and an ultrasound imaging and tracking circuit 170 coupled to each transducer 152 in the ring array 160 for performing RF (radio frequency) data acquisition with the plurality of ring-arrayed transducers 152. Imaging logic 172 includes a set of processor based instructions for performing the imaging as described above for rendering the image 140 based on the signals 252.

A needle holster 130 is concentrically disposed in the ring array 160 and is adapted to receive and direct an insertion instrument such as needle 110 along an axis 111 defined by a center 164 of the ring array 160 and aligned or nearly aligned with the surgical target 134. A rotary encoder 174 is responsive to rotation of the ring 150 for providing the rotational position to the tracking circuit 170. Any suitable mechanism for identifying and reporting the rotation may be provided.

In the configuration as shown, the circular array 150 has a center axis 111 defining a radius 180 to each of the transducers 152. The plurality of transducers 152 is disposed in the circular frame 150 to define the circular array 160, such that the transducers 152 are centered around the needle insertion sheath 130 defining the needle axis 111. The tracking circuit 170 computes each pixel on the rendered image 140 from a value based on a distance 136 from the location on the reconstruction plane 132 to each respective transducer 152, such that the distance is computed based on the radius. Each location corresponding to a pixel also has an angle 137 from the transducer 152 and a depth 138, which is a function of the angle 137 and distance 136, which define a location on the reconstruction plane 132. In the circular array 160, the radius will be the same to each transducer, however in alternate configurations, the circular frame 150 may take an elliptical or oval form, in which it further comprises a major axis and a minor axis. Elliptical considerations may also occur based on a tilting of the sheath 130 that draw the array 150 off of a true perpendicular or normal path to the target 134.

Figure 5:
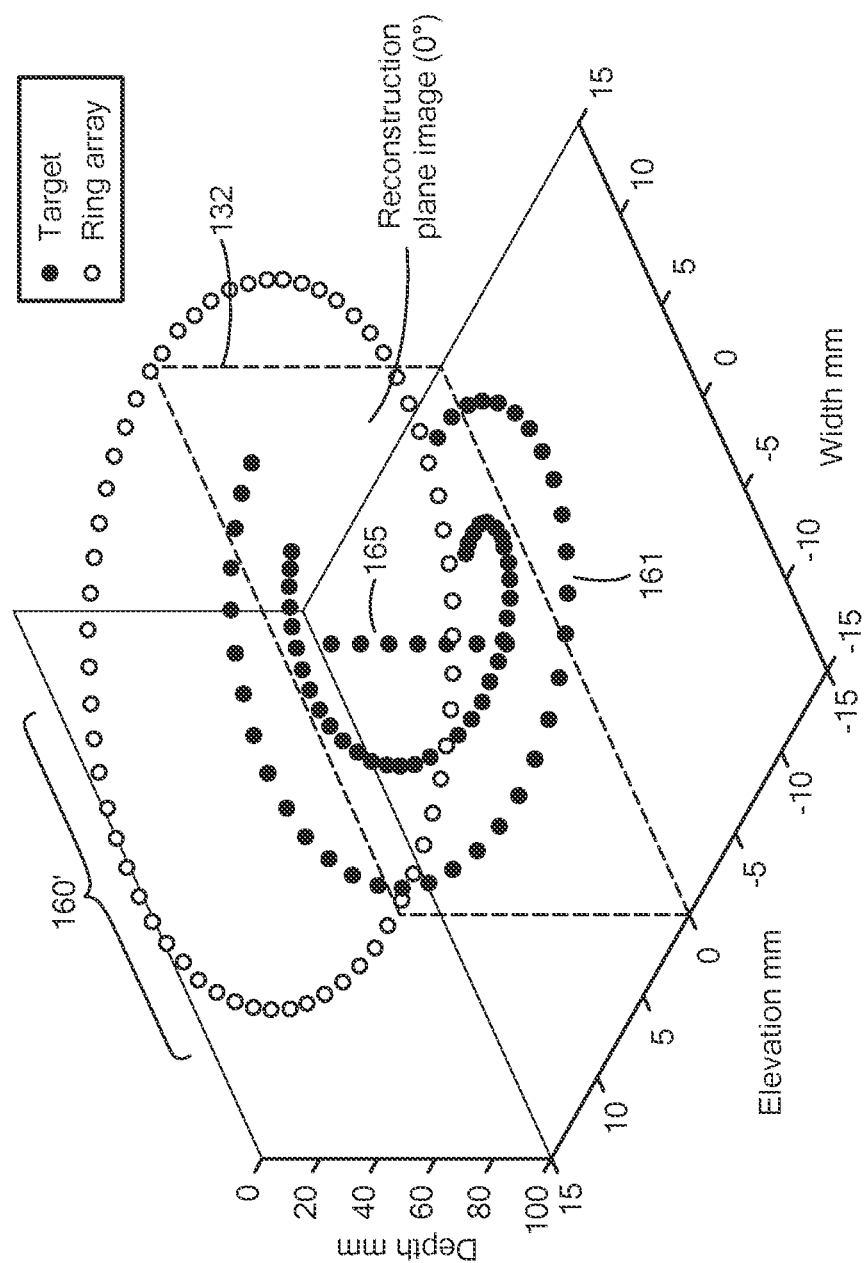
FIG. 5 shows example point targets of imaging in the system of FIG. 4.

FIG. 5 shows example point targets of imaging in the system of FIG. 4. Referring to FIGS. 3-5, the transducer 152 locations 160' of the circular array 160 are shown aligned with the uppermost boundary of the reconstruction plane 132, defining 0 degrees of rotation. Sensing locations are shown as a downward spiral 161 of imaged locations, having increasing depth based on a range 165 of target depth. The tracking circuit 170 receives a rotation signal, such that the rotation signal is based on the encoder 174 in rotary communication with the circular frame 150. Depending on the rotation, the tracking circuit 170 may identify a second reconstruction plane based on the rotation signal, as the relative transducer position to the reconstruction plane 132 moves one or more transducer positions 160'. The tracking circuit 170 then renders an image 140 based on the second reconstruction plane, representing a shift of one or more transducer positions 160.'

Figure 6:
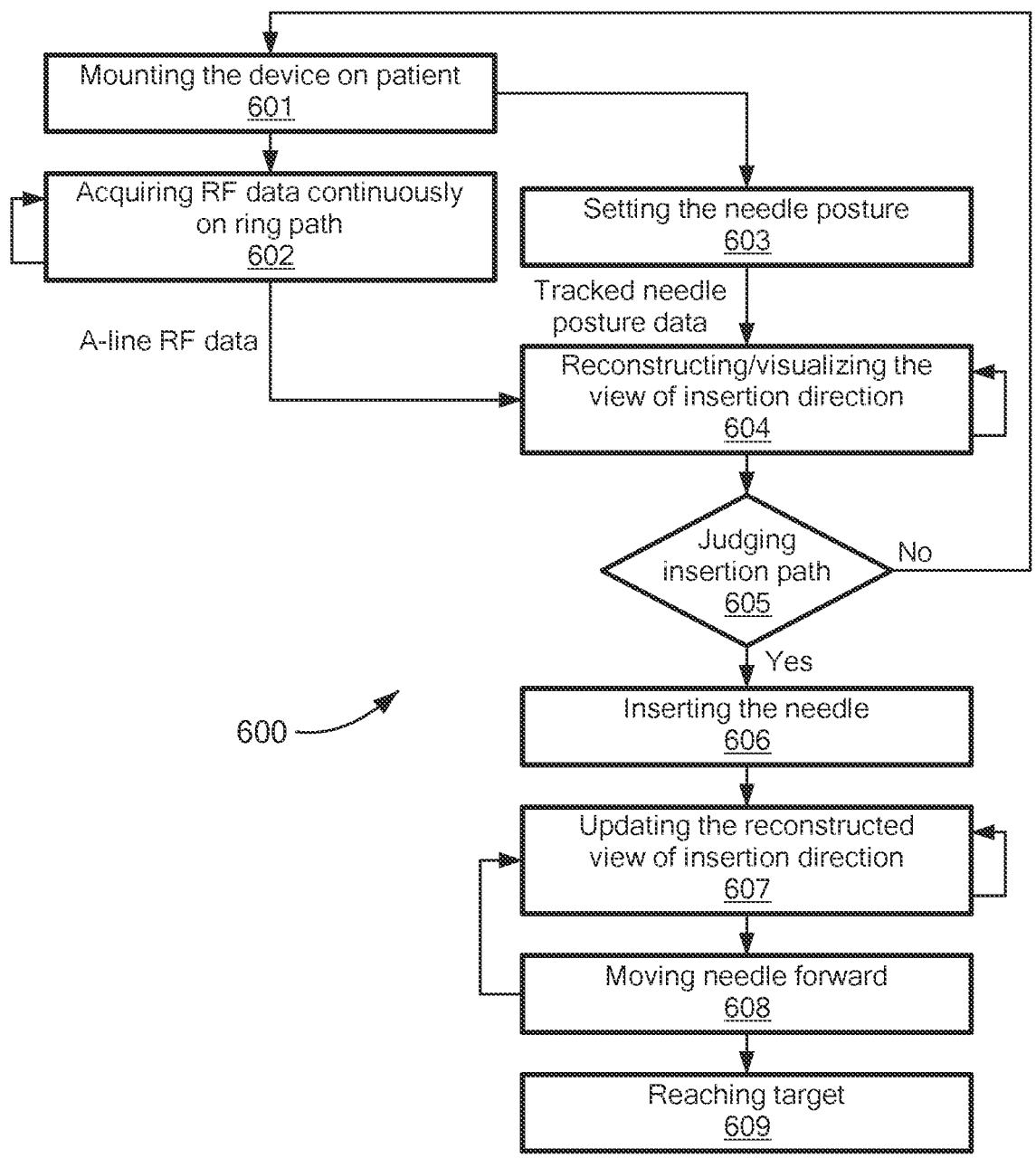
FIG. 6 shows a flowchart for imaging using the system of FIG. 4.

FIG. 6 shows a flowchart for imaging using the system of FIG. 4. Referring to FIGS. 1-6, a flowchart 600 depicts a sequence for generating the image 140. At step 601, the imaging device 104 is disposed on the patient 114 at a location deemed above the target location 134 for mounting device 104. After mounting the device 104, RF data is collected continuously from the ring-arrayed transducers 152, shown at step 602 while the needle posture is set by rotating the device 104, as depicted at step 603. The forward-viewing US images 140 are reconstructed and rendered based on the needle posture, as disclosed at step 604, based on emission of an ultrasonic (US) beam from each of the transducers 152 around the circular array 160. The rendered image 140 may be employed to evaluate an acceptable insertion path directly by changing the (rotation) needle posture or shifting the device on the body surface 112 in a slidable manner, depicted at step 605 and performed iteratively until an acceptable path axis 111 is found. Once an acceptable needle 110 insertion path is found, the needle angle will be fixed and insertion commenced, as shown at step 606. The rendered forward-viewing image 140 continually updates in real-time during the needle insertion for tracking the needle location 607 as the needle advances towards the target 134 along the axis 111, depicted at step 608. The tracking circuit 170 continues to render the generated image along a forward direction of needle insertion, until the target is attained at step 609.

In operation, as the device 304 is positioned and the needle 110 advanced, the transducers 152 emit and receiving a return signal at each emitting transducer or a combination of multiple transducers in proximity to the emitting transducer. Each transducer is a single element transducer operable for transmission and reception of US signals. The tracking circuit 170 computes, based on each of a plurality of positions on the reconstruction plane 132, a value for the corresponding pixel based on the return signal from a plurality of the transducers 152. In other words, the transducers emit 252 and receive signals 252' in an iterative manner for the depth and width of the reconstruction plane 132. For each scanned or imaged position on the reconstruction plane, the tracking circuit receives and evaluates a return signal 252' to compute a value of a corresponding pixel in the rendered image 140, as disclosed above with respect to FIG. 4. The tracking circuit 170 iterates over a plurality of positions on the reconstruction plane 132 for computing a value for a corresponding pixel of each pixel of the generated image 140. Each transducer 152 receives the return signal 252' based on a depth, distance and angle to the corresponding location on the reconstruction plane 132 from the respective transducer 152.

Figure 7:
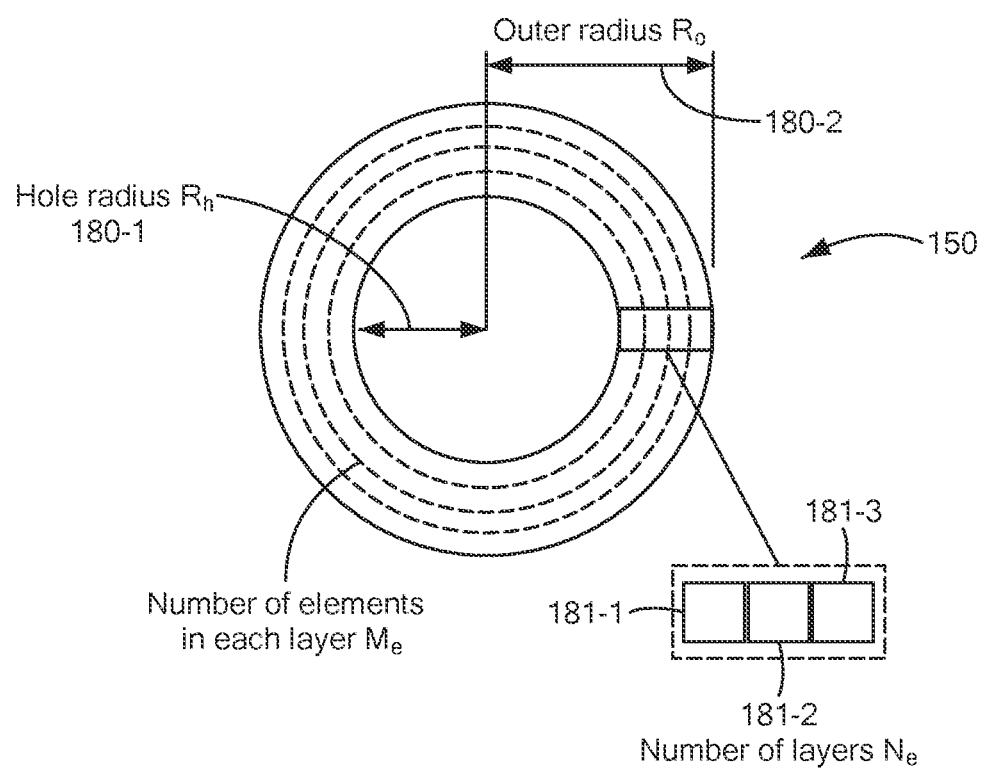
FIG. 7 shows an alternate arrangement of the transducers of FIGS. 2A and 2B using concentric rings of transducers.

FIG. 7 shows an alternate arrangement of the transducers of FIGS. 2A and 2B using concentric rings of transducers. Referring to FIGS. 1-7, the circular frame 150 may have multiple concentric arrays 160-1 . . . 160-N of transducers 152. Each of the transducers 152 defines a radius based on a distance to the center of the circular frame, such that all transducers of a first ring have an equal radius, and all transducers of an outer ring have an equal but greater radius than the first or innermost ring.

The frame 150 disposes the transducers 152 according to a plurality of radii 180-1 . . . 180-2 (180 generally) around the circular frame 150, and generates the image 140 from a distance to each of the plurality of positions on the reconstruction plane 132, and an angle 137 defined from the circular frame to the respective position. Each of the concentric rings therefore defines a layer 181-1 . . . 181-3 (181 generally) according to the incremental radii. In the multi-ring approach of FIG. 7, design parameters of the ring array configuration are mainly considerable as following: 1) the hole radius $R_h$, 2) the outer radius of whole ring array $R_o$, 3) the total number of transducer elements E, 4) the number of ring layer $N_e$, and 5) the number of transducer element in each ring layer $M_e$ as shown in FIG. 7. Given that the transducer elements 152 are equally spaced in the array 150 plane, the position of each transducer element e can be defined in a polar coordinate system as following:

$$e(r,\theta)=(R_h+n_e d_r, m_e d_\theta)$$

$$n_e=1 \ldots N_e$$

$$m_e=1 \ldots M_e$$

$$E=N_e M_e$$

where $d_r$ and $d_\theta$ represent the pitch distance of each transducer element along the radical direction and the pitch angle of each transducer in each ring layer, and $n_e$ and $m_e$ represent the layer number and transducer element number in the ring layer. $d_r$ and $d_\theta$ are also determined as following:

$$d_r = \frac{R_o - R_h}{N_e}$$

$$d_\theta = \frac{2\pi}{M_e}$$

The conceptual result is merely that the central void or "hole" at which the needle axis 111 is centered varies in size.

Figure 8A:
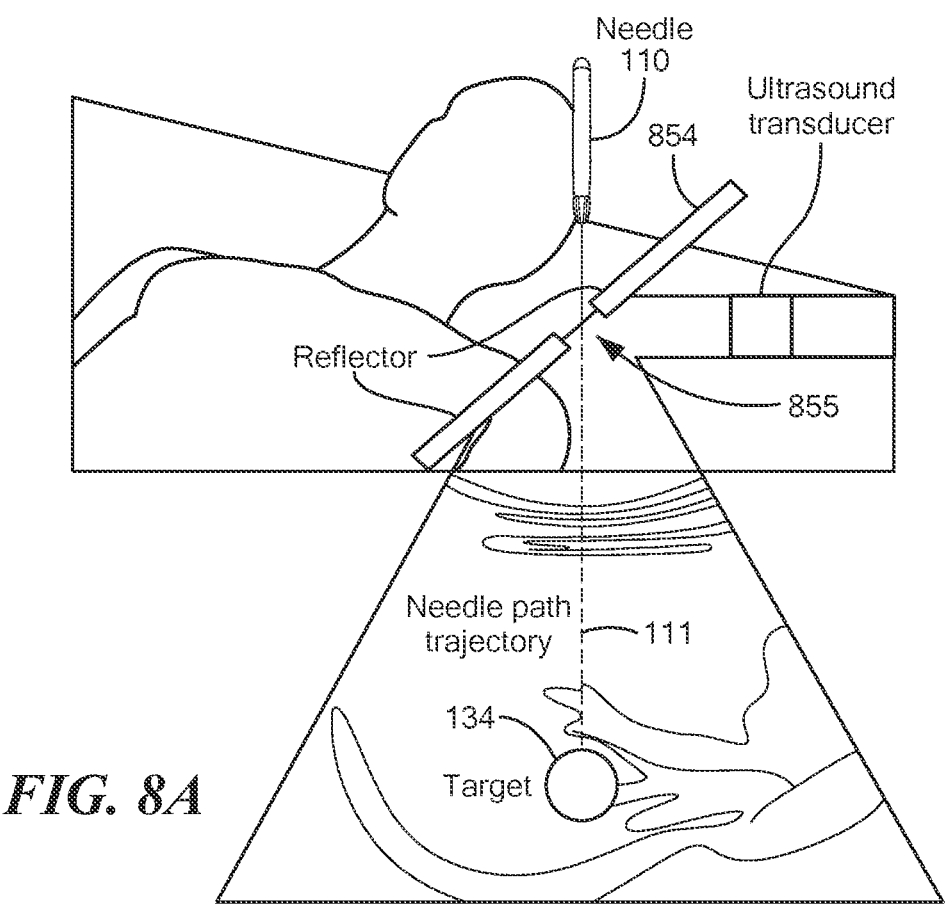
FIGS. 8A and 8B show an alternate configuration employing an acoustic mirror for enhancing imaging along a needle axis in the system of FIG. 4.
Figure 8B:
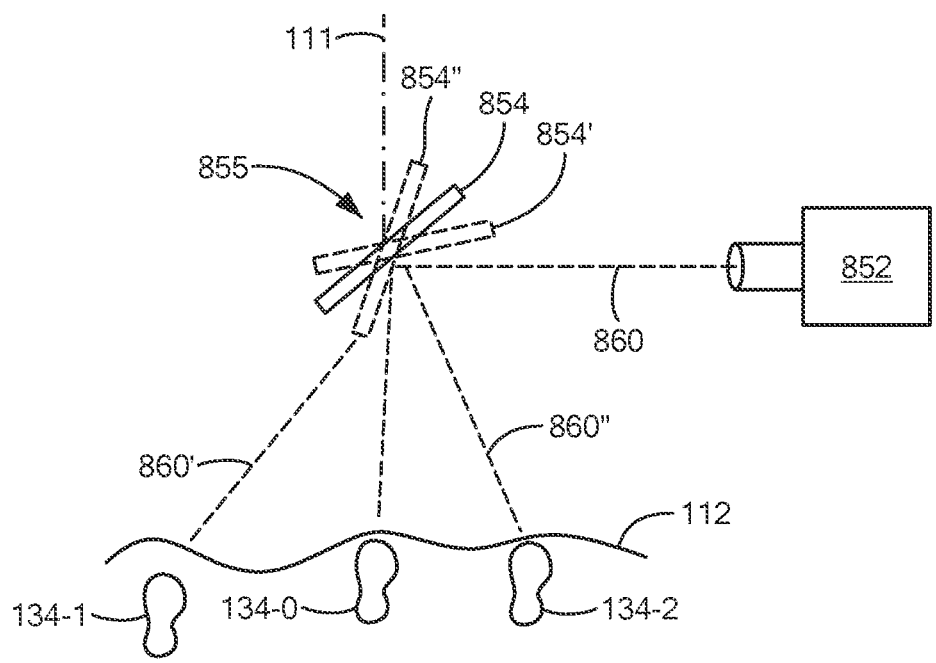

FIGS. 8A and 8B show an alternate configuration employing an acoustic mirror for similar operation in conjunction with the ring array, and further enhancing imaging along a needle axis in the system of FIG. 4. Referring to FIGS. 4, 8A and 8B, an indirect transducer 852 is attached to a crossmember 800 extending across the frame 150. The reflective surface of the mirror 854 and transducer can rotate and translate to capture 3D volume and provide equivalent information, possibly in conjunction with the array 160. An acoustic mirror 854 is disposed at an angle (typically 45°) adjacent the needle sheath 130. The acoustic mirror 854 is disposed at a center of the circular frame 150, such that the reflective mirror has a surface responsive to the signals for reflecting the signals onto the reconstruction plane 132 based on an angle of the mirror. The mirror 854 has an aperture or hole 855 for allowing passage of the needle 110, such that the hole is sufficiently small that it will not interfere substantially with the emitted and return signal, but allows redirection of the signals aligned or substantially aligned with the needle axis 111. The needle 110 is thus received through the aperture 855 in the mirror; and the tracking circuit 170 generates the image 170 based on coalescing the reflected signals with the received set of signals. The transducer 852 is disposed in proximity to the mirror 854, either on the crossmember 800 or coupled via an optical fiber, and transmits a signal horizontally at the 45° mirror for achieving a 90° reflection parallel to the reconstruction plane 132.

FIG. 8B illustrates reflection of the signal emitted from the transducer 852 as beam 860 and directed towards the servo-operated mirror 854, Depending on activation of the servo motor, the mirror 854 is rotatable to a variety of positions such as 854' and 854" for reflecting the beam 860 to different tissue regions. In particular configurations, the transducer 852 may also be translated and rotated by actuators, such as for generating a corn beam. Alternate surgical targets 134-0 . . . 134-2 beneath the epidermal surface 112 can be imaged by the beam 869 based on the position of the mirror 854 in response to rotation by the servo motor. A single dimension is shown, but rotation in two dimensions may be achieved by disposing the mirror 854 in a frame or assembly such as a gimbal.

In FIG. 8B, rotation of the mirror to an angle defined by 854' reflects the beam 860' to surgical target 134-1. Similarly, a tighter (more acute) angle is achieved by an angle defined by 854", reflecting the beam 860" towards surgical target 134-2. Larger scan areas may be covered with fewer transducers by having the beam 860 image regions in succession such as 134-0, 134-1 and 134-2.

Further enhancements can be achieved by motorizing translation and rotation of the transducer 852 and bending the ultrasound beam to cover the intended reconstruction area utilizing an acoustic mirror 854 as reflector. The reflector is positioned in front of the array with an angle to reflect the forward-shot US beam. Hence, given that the relative angle between the 1D array and reflector is set at 45°, the forward-shot US beam can be reflected 90°. This approach provides a variable angled B-mode slice based on the adjustment of the relative angle and position between the array and reflector, and the volumetric image can be formed as a composition of serial B-mode slice consecutively acquired through the translational and rotational motions of the 1D array and reflectors. High resolution 3D imaging can be achieved in this configuration by incorporating out-of-plane synthetic aperture beamforming.

Figure 9:
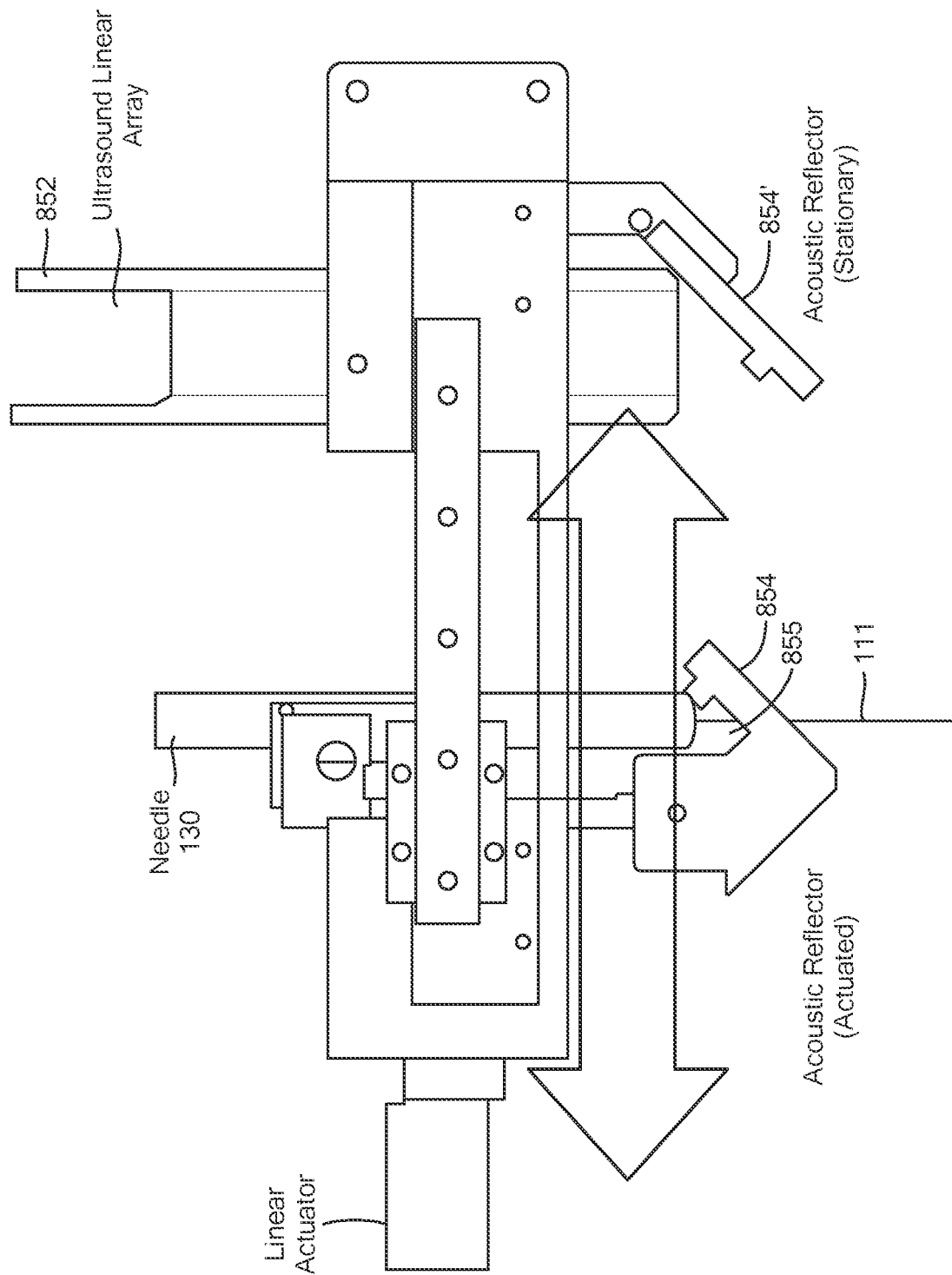
FIG. 9 shows manipulation of the acoustic mirror of FIGS. 8A and 8B for generating an image.

FIG. 9 shows manipulation of the acoustic mirror of FIGS. 8A and 8B for generating an image. The mirror 854 enhances visualization of the forward-view of needle insertion by utilizing a 1D linear array transducer 852' to emit and receive the US beam and an acoustic reflector 854. In the example shown, the transducer 852' may be a single element, as in 152 above, or an array. The emitted beam is reflected first by preliminary mirror 854' along a horizontal path normal to the needle axis 111, then reflected again at the needle 110 by the mirror 854 along the needle axis 111, such that the needle 110 passes through the aperture 855 and onward to the surgical target 134. Actuated movement and angling (rotation) of the mirrors allow imaging of larger regions as the transducer beam is redirected over the imaged area.

Those skilled in the art should readily appreciate that the programs and methods defined herein are deliverable to a user processing and rendering device in many forms, including but not limited to a) information permanently stored on non-writeable storage media such as ROM devices, b) information alterably stored on writeable non-transitory storage media such as solid state drives (SSDs) and media, flash drives, floppy disks, magnetic tapes, CDs, RAM devices, and other magnetic and optical media, or c) information conveyed to a computer through communication media, as in an electronic network such as the Internet or telephone modem lines. The operations and methods may be implemented in a software executable object or as a set of encoded instructions for execution by a processor responsive to the instructions, including virtual machines and hypervisor controlled execution environments. Alternatively, the operations and methods disclosed herein may be embodied in whole or in part using hardware components, such as Application Specific Integrated Circuits (ASICs), Field Programmable Gate Arrays (FPGAs), state machines, controllers or other hardware components or devices, or a combination of hardware, software, and firmware components.

While the system and methods defined herein have been particularly shown and described with references to embodiments thereof, it will be understood by those skilled in the art that various changes in form and details may be made therein without departing from the scope of the invention encompassed by the appended claims.

What is claimed is:

1. A method for generating an image of scanned tissue, comprising:
    receiving a set of signals from a circular array of transducers, the circular array defined by a circular frame having the transducers disposed thereon, the circular array having a center defining a radius to each of the transducers;
    identifying a reconstruction plane defined by a rotational position of the circular array, the signals in the set of signals emitted by and returning to each transducer in the circular array of transducers at an angle based on the rotational position;
    aligning the reconstruction plane with a center of the circular array based on a needle positioning sheath adapted to slidably receive a needle for directing the needle to a target location depicted on a generated image;
    receiving a needle through the needle positioning sheath, the needle defining the reconstruction plane;
    generating the image based on the received set of signals by reconstructing, for each of a plurality of locations on the reconstruction plane, a corresponding pixel based on a signal in the set of signals received from each of the transducers by computing each pixel from a value based on a received return signal from the location on the reconstruction plane to the transducer, the return signal based on a depth, distance and angle of the rotational position to the corresponding location on the reconstruction plane from the respective transducer, the distance computed based on the radius and the respective angle of the rotational position;
    rotating the circular array of transducers according to a second angle based on rotational position movement of the circular frame; and
    generating a second image based on a second reconstruction plane defined by the second angle, depth and distance to a corresponding location on the second reconstruction plane while maintaining an insertion depth of the needle.

2. The method of claim 1 further comprising disposing a plurality of the transducers in the circular frame to define the circular array, the transducers centered around the needle positioning sheath.

3. The method of claim 2 further comprising:
    receiving a rotation signal indicative of the second angle, the rotation signal based on an encoder in rotary communication with the circular frame; and
    identifying the second reconstruction plane based on the rotation signal; and
    rendering the second image based on the second reconstruction plane.

4. The method of claim 2 further comprising rendering an image of a surgical target, the surgical target located on the reconstruction plane and based on an insertion site aligned with a needle on a trajectory defined by the needle positioning sheath.

5. The method of claim 1 further comprising:
    rendering the generated image along a forward direction of needle insertion, further comprising:
    emitting an ultrasonic (US) beam from each of the transducers around the circular array;
    receiving a return signal at the emitting transducer, each transducer operable for transmission and reception of US signals;
    computing, based on a location on the reconstruction plane, a value for the corresponding pixel based on the return signal from a plurality of the transducers;
    iterating over a plurality of locations on the reconstruction plane for computing a value for a corresponding pixel of each pixel of the generated image.

6. The method of claim 5 wherein the target location and the needle are aligned with the reconstruction plane and visualized on the generated image.

7. The method of claim 1 further comprising:
disposing a reflective mirror at a center of the circular frame, the reflective mirror having a surface responsive to the signals for reflecting the signals based on an angle of the reflective mirror;
receiving the needle through an aperture in the reflective mirror; and
generating the image based on coalescing the reflected signals with the received set of signals.

8. The method of claim 7 further comprising disposing at least one transducer in proximity to the reflective mirror, and receiving the reflected signals at the transducer in proximity to the reflective mirror.

9. The method of claim 8 further comprising actuating the reflective mirror based on an angle and position, the angle and position based on a target position for imaging.

10. The method of claim 1 wherein each of the transducers defines a radius based on a distance to the center of the circular frame, further comprising:
disposing the transducers according to a plurality of radii around the circular frame; and
generating the image from a distance to each of the plurality of locations on the reconstruction plane, and an angle defined from the circular frame to the respective location.

11. A Ring-Arrayed Forward-viewing (RAF) ultrasound imaging and administration device, comprising:
an ultrasonic (US) imager including a plurality of single element transducers arranged in a circular frame to define a circular ring array, the circular ring array having a center defining a radius to each of the transducers;
an instrument posture tracking circuit electrically coupled to the transducers on the circular ring array for performing RF (radio frequency) data acquisition with the plurality of ring-arrayed transducers and acquiring RF data, the RF data based on signals emitted by and returning to each transducer in the circular ring array of transducers, each transducer at an angle and radius based on a rotational position of the circular ring array;
an insertion instrument adapted for percutaneous insertion;
a needle holster concentrically disposed in the circular ring array and adapted to receive and direct the insertion instrument along an axis defined by a center of the circular ring array;
a generated image based on a reconstruction plane aligned with a center of the circular ring array based on the needle holster adapted to slidably receive the insertion instrument for directing the insertion instrument to a target location depicted on the generated image, the insertion instrument defining the reconstruction plane;
the acquired RF data indicative of pixels on the reconstruction plane by computing each pixel from a value based on a received return signal from a respective location on the reconstruction plane to the transducer, the return signal based on a depth, distance and angle of the rotational position to the corresponding location on the reconstruction plane from the respective transducer the distance computed based on the radius and the respective angle of the rotational position;
the circular ring array adapted for rotation to a second angle based on rotational position movement of the circular frame; and
a second image generated based on a second reconstruction plane defined by the second angle, depth and distance to a corresponding location on the second reconstruction plane while maintaining an insertion depth of the needle.

12. The device of claim 11 wherein the instrument posture tracking circuit includes instructions for tracking an instrument posture and US image reconstruction along a direction of forward insertion of the insertion instrument based on the acquired RF data with a back-propagation method and based on the tracked instrument posture.

13. The device of claim 12 wherein the needle holster is mechanically fixed to the center of the ring-arrayed transducers for receiving the insertion instrument such that a positional relationship between the advancing insertion instrument and the reconstructed US image is kinematically fixed.

14. The device of claim 12 wherein the instrument posture tracking circuit is configured for reconstructing a B-mode US image along a radial slice, the radial slice defined by the gathered RF data, with the ring-arrayed transducers, such that a forward-viewing image of needle insertion based on the center of the US image is matched to the needle insertion path to define the reconstructed image.

15. The method of claim 1 wherein the signals in the set of signals are bidirectional ultrasonic signals.

16. The method of claim 4 wherein the signals define a reconstructed image including the surgical target for each angle defined by the transducers in the circular array.

17. The method of claim 1, wherein the circular array of transducers further includes a plurality of concentric rings, each concentric ring of the plurality of concentric rings having a circular array of transducers at a common radii, further comprising receiving return signals at transducers disposed on each ring of the plurality of concentric rings.

* * * * *